(12) United States Patent
Bjorkholm

(10) Patent No.: US 6,301,326 B2
(45) Date of Patent: *Oct. 9, 2001

(54) SHEET DETECTION SYSTEM

(75) Inventor: Paul J. Bjorkholm, Newport Beach, CA (US)

(73) Assignee: PerkinElmer Detection Systems, Inc., Cypress, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,629

(22) Filed: Nov. 2, 1998

(51) Int. Cl.⁷ ................................................. G01N 23/04
(52) U.S. Cl. .............................. 378/57; 378/51; 378/53; 378/54; 378/55
(58) Field of Search ............................ 378/57, 51, 53, 378/54, 55

(56) References Cited

U.S. PATENT DOCUMENTS

| | | | |
|---|---|---|---|
| 4,029,963 | * 6/1977 | Alvarez et al. | 378/5 |
| 4,349,740 | * 9/1982 | Grassmann et al. | 378/25 |
| 5,237,598 | * 8/1993 | Albert | 378/98.6 |
| 5,319,547 | 6/1994 | Krug et al. | 705/13 |
| 5,442,672 | 8/1995 | Bjorkholm et al. | 378/4 |
| 5,479,023 | * 12/1995 | Bartle | 250/390.04 |
| 5,638,420 | * 6/1997 | Armistead | 378/57 |
| 5,642,393 | * 6/1997 | Krug et al. | 378/57 |
| 5,818,897 | * 10/1998 | Gordon | 378/19 |
| 5,838,759 | * 11/1998 | Armistead | 378/57 |
| 5,970,113 | * 10/1999 | Crawford et al. | 378/19 |
| 6,026,143 | * 2/2000 | Simanovsky et al. | 378/57 |
| 6,035,014 | * 3/2000 | Hiraoglu et al. | 378/57 |
| 6,088,423 | * 7/2000 | Krug et al. | 378/57 |
| 6,167,113 | * 12/2000 | Armentrout et al. | 378/54 |

OTHER PUBLICATIONS

Grodzins, L., "Photons in—Photons Out: Non–Destructive Inspection of Containers Using X–Ray and Gamma Ray Techniques", Proceedings of the 1st International Symposium on Explosive Detection Technology, pp. 201–225, Nov. 1–15, 1991.

Kuauss et al., "Signatures of Explosives by Elemental Composition Analysis", Proceedings of the 2nd Explosive Detection Technology Symposium & Aviation Securitiy Technology Conf., Nov. 12–15, 1996.

* cited by examiner

Primary Examiner—Robert H. Kim
Assistant Examiner—Allen C. Ho
(74) Attorney, Agent, or Firm—Iandiorio & Teska

(57) ABSTRACT

A detection system for detecting sheets of material includes a device for moving along a path a container which can harbor a sheet of material sought to be detected; an X-ray scanner having a beam for scanning across the path of the container through a predetermined angle and a device for moving the scanner to shift the origin of the scanning beam to align during at least a portion of the scan the scanning beam with the sheet for producing a high projected density contrasted with its surroundings.

18 Claims, 8 Drawing Sheets

SHEET DETECTION SYSTEM

FIELD OF INVENTION

This invention relates to a detection system for detecting thin sheets of material, and more particular to a system for detecting sheets of organic material including contraband materials such as drugs and explosives.

BACKGROUND OF INVENTION

There are a number of different techniques for detecting objects in closed containers such as suitcases and boxes carried by airplanes which involve conveying the suitcases past an X-ray scanner. In particular, contraband such as drugs or explosive materials are sought to be detected by discerning their densities and/or atomic number using dual energy approaches. The dual energy atomic number approach relies on the fact that when an X-ray beam strikes material the energy of the beam is diminished either because of absorption (the photoelectric effect $\mu_{pe}$) or because of scattering (the Compton scattering effect $\mu_{cs}$) and that the probability of the photoelectric effect, $\mu_{pe}$, changes markedly with increased energy while the compton scattering, $\mu_{cs}$, does not. Since $\mu_{pe}$ is a function of atomic number/energy and $\mu_{es}$ is a function of atomic mumber, these expressions can be solved for atomic number by using two different X-ray energy levels, e.g., 40 Kev and 90 Kev. In the case of explosives the materials sought are organic, containing carbon, nitrogen and oxygen, and have an atomic number of around 7. Heavier metals such as iron and chromium often found in luggage have atomic numbers of 28 or higher, and aluminum and chlorine have atomic numbers of around 12. Therefore, there is a comfortable margin for detection of the organic explosives. See "Device and Method for Inspection of Baggage and Other Objects", Krug et al., U.S. Pat. No. 5,319,547.

Density is also used to detect explosives because they typically have a density of 1.2–1.9 gm/cm$^3$ for military and 1–1.4 gm/cm$^3$ for commercial grade explosives which are well separated from the densities of other materials commonly found in luggage. Since a single dimension X-ray system can only produce a two dimensional or areal density, that is, weight per unit area related to the projected area of an object, it is not entirely reliable: the projected density is a composite of all densities in the line of the X-ray beam and one material can mask another. To overcome this and other shortcomings a three-dimensional scanner was developed. See "Three-Dimensional Reconstruction Based on a Limited Number of X-Ray Projections", Bjorkholm et al., U.S. Pat. No. 5,442,672.

But even this approach is subject to failure when thin sheets of explosive or other contraband are imaged perpendicularly or transversely relative to the sheet. A sheet imaged on edge, i.e., aligned with a scanning beam, is highly contrasted and detectable but when it is crosswise or wholly perpendicular to the scanning beam its thin dimension gives a very low areal density, e.g., less than 1 gm/cm, easily obscured when combined with the other objects in the line of sight. Such sheets of material are most likely to be disposed or secreted in the broad sides of a suitcase, not in the narrower ends or top and bottom, so they are not likely to be seen on edge. The only present technique for detecting these sheets with good reliability are computerized axial tomography systems which are large, complex and expensive.

SUMMARY OF INVENTION

It is therefore an object of this invention to provide an improved detection system which can detect thin sheets of material.

It is a further object of this invention to provide such a detection system which can detect thin sheets of organic material.

It is a further object of this invention to provide such a detection system which can detect thin sheets even when they are aligned in the broad sides of a container or luggage.

It is a further object of this invention to provide such a detection system which is simple and inexpensive and requires no complicated solutions.

The invention results from the realization that a truly effective detection system capable of exposing even a thin sheet of contraband such as explosives or drugs hidden density in a container can be achieved by shifting the X-ray source as it scans so that at at least one point the X-ray beam will align with a contraband sheet in one of its possible orientations in the container producing a high contrast, highly detectable edge-on view.

This invention features a detection system for detecting sheets of material. There are means for moving along a path a container which can harbor a sheet of material and an X-ray scanner having a scanning beam for scanning across the path of the container through a predetermined angle. There are means for shifting the origin of the scanning beam to align during at least a portion of the scan the scanning beam with the sheet for producing a high projected density contrasted with its surroundings.

In a preferred embodiment the X-ray scanner may include an X-ray source and a spaced detector and the means for shifting may include a movable member for supporting the source and the detector. Alternatively, the X-ray scanner may include an X-ray source and a spaced detector and may include the means for shifting may include a movable member for supporting the source. The X-ray scanner may include an X-ray source including a plurality of individual sources and said means for shifting may include means for sequentially enabling the individual sources. The X-ray scanner may include a linear X-ray anode and said means for shifting may include means for sweeping an electron beam across the anode for generating a series of X-ray scanning beams. The X-ray scanner may include a detector for detecting X-ray energy transmitted by the sheet. The X-ray scanner may include means for determining whether the X-ray energy detected from the sheet represents an areal density within a target envelope of areal densities. The X-ray scanner may include a threshold detector for determining whether the areal density representative of the sheet exceeds a predetermined level. The detector may include a dual energy detector for detecting high and low X-ray energies. The means for determining may include a look-up table of stored areal densities within the target envelope. The X-ray scanner may include a storage device for storing areal densities representing a set of scans of the sheet. The X-ray scanner may include an envelope comparator for determining whether the areal density which exceeds the threshold represents an atomic number indicative of a sheet of the particular material sought. The X-ray scanner may include an angular response circuit for determining the angular response of a set of scans. The angular response circuit may include means for determining symmetry in the areal density of scans surrounding a scan which exceeds the threshold level to confirm the presence of a sheet. The angular response circuit may include means for determining the slope of the angular response of the areal densities of a set of scans indicative of the presence of a sheet of material. The X-ray scanner may provide a fan beam of X-ray energy.

DISCLOSURE OF PREFERRED EMBODIMENT

Other objects, features and advantages will occur to those skilled in the art from the following description of a preferred embodiment and the accompanying drawings, in which.

DETAILED DESCRIPTION OF PREFERRED EMBODIMENTS

Figure 1:
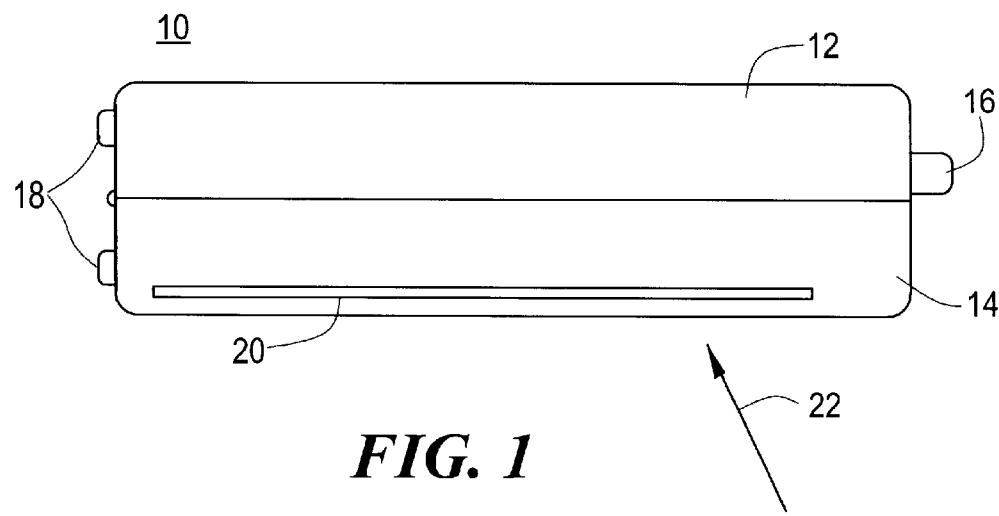
FIG. 1 is a schematic side elevational view of a suitcase harboring a sheet of material being imaged by an X-ray scan generally perpendicular to the sheet, wherein detection is unlikely.
Figure 2:
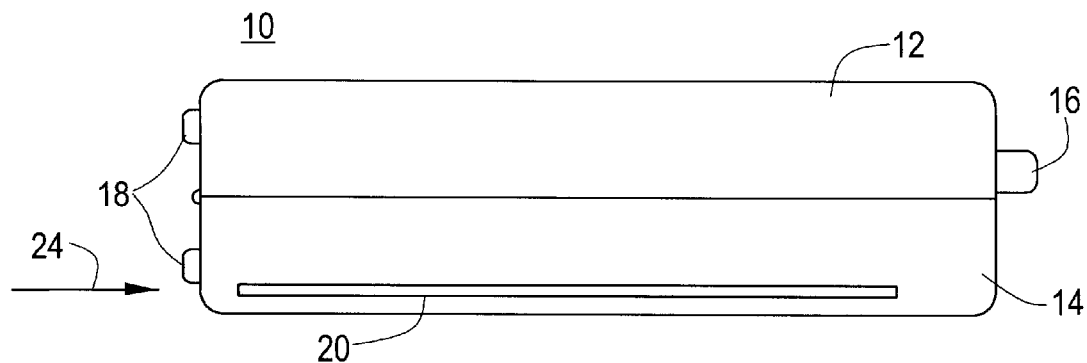
FIG. 2 is a view similar to FIG. 1 with the sheet being imaged end-on by the X-ray scan where detection is most likely.
Figure 3:
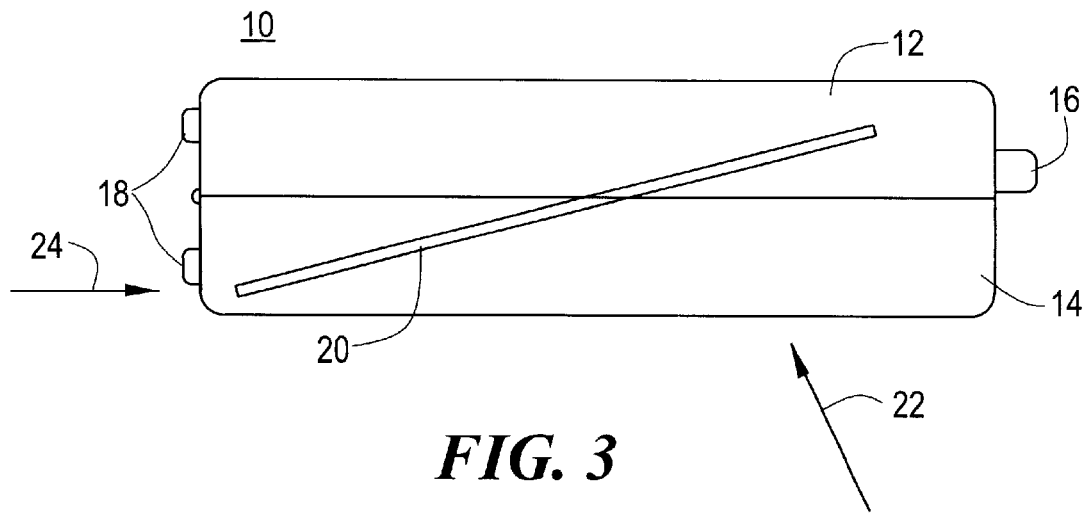
FIG. 3 is a view similar to FIGS. 1 and 2 with the sheet being imaged at an angle to two differently oriented X-ray scans wherein detection is unlikely.

There is shown in FIG. 1 a typical suitcase 10 having two hingeably connected halves 12 and 14, a handle 16 and feet 18. Contained in suitcase 10 is a sheet of material 20 which is to be detected. Sheet 20, which may be drugs or an explosive, would typically have a projected or areal organic thickness of less than 0.8 gm/cm$^2$ when viewed by beam 22 oriented perpendicularly or at least transversely to sheet 20. Normally a suitcase would have approximately 10 gm/cm$^2$ organic material or more and there would be large variations. Thus the low areal density which occurs when thin sheet 20 is viewed by a transverse X-ray beam 22 is easily hidden amongst the other material in the suitcase and is not likely to be detected. However, if an X-ray beam 24, FIG. 2, is oriented so that it is end-on to sheet 20, then the projected density could be more than 30 gm/cm$^2$ which would likely result in a detection. However, this is a very low probability occurrence even when the X-ray scanning system is a three-dimensional or Z-axis scanning system such as disclosed in U.S. Pat. No. 5,542,672, for sheet 20 may not always be oriented parallel to the broad flat sides of the suitcase but may be inclined as shown in FIG. 3 so that both X-ray beams 22 and 24 strike it transversely and neither produces the end-on high contrast view which is likely to be detected.

Figure 4:
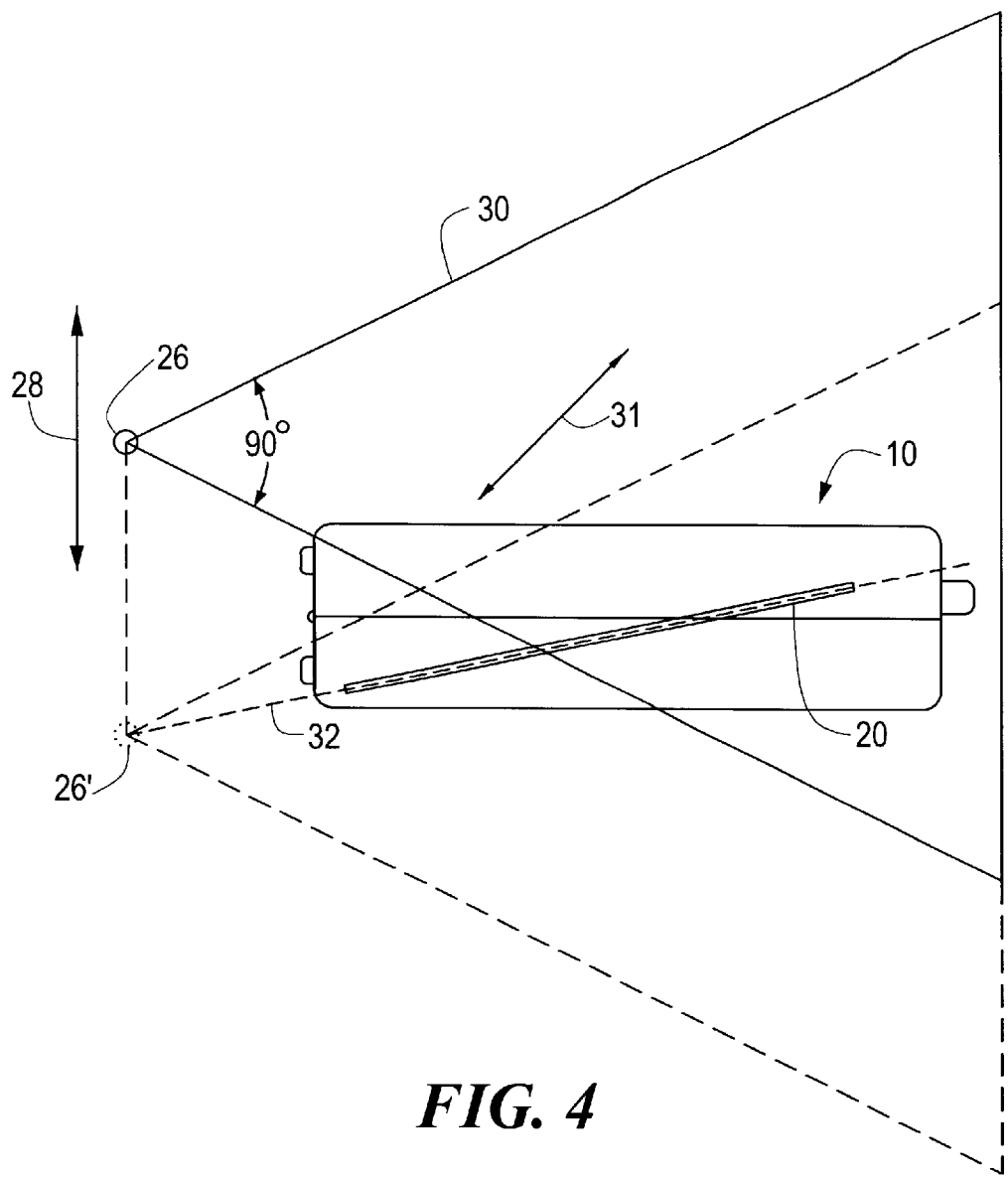
FIG. 4 is a view similar to FIGS. 1–3 in which the X-ray source is moved to align at some point the X-ray beam with the sheet, according to this invention.

In accordance with this invention, as suitcase 10, FIG. 4, moves along an axis either into or out of the paper, and source 26 is shifted or moved up and down in the direction of arrow 28, at some point a beam of energy 32 from source 26 will align for an end-on view with sheet 20. The typical threshold detection level is around 15 gm/cm$^2$; the typical X-ray beam power is from 40–150 Kev and the scan beam is typically 90°.

Figure 5:
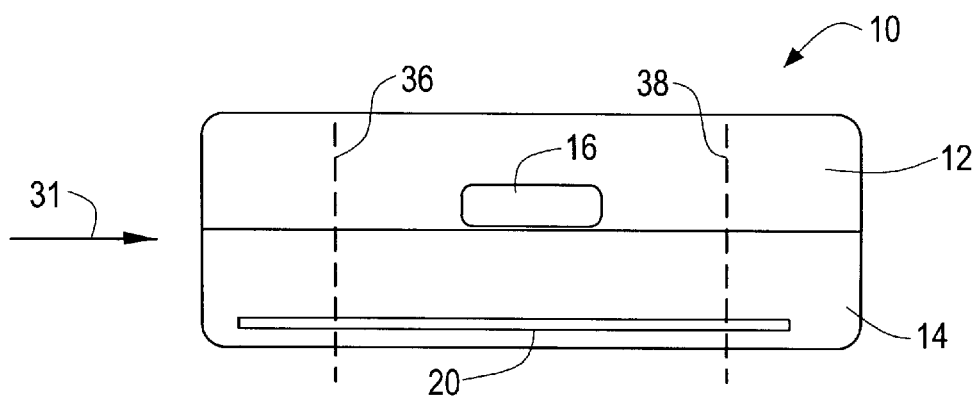
FIG. 5 is a view similar to FIGS. 1–4 illustrating the spacing between scans to ensure interception of a sheet material.
Figure 6:
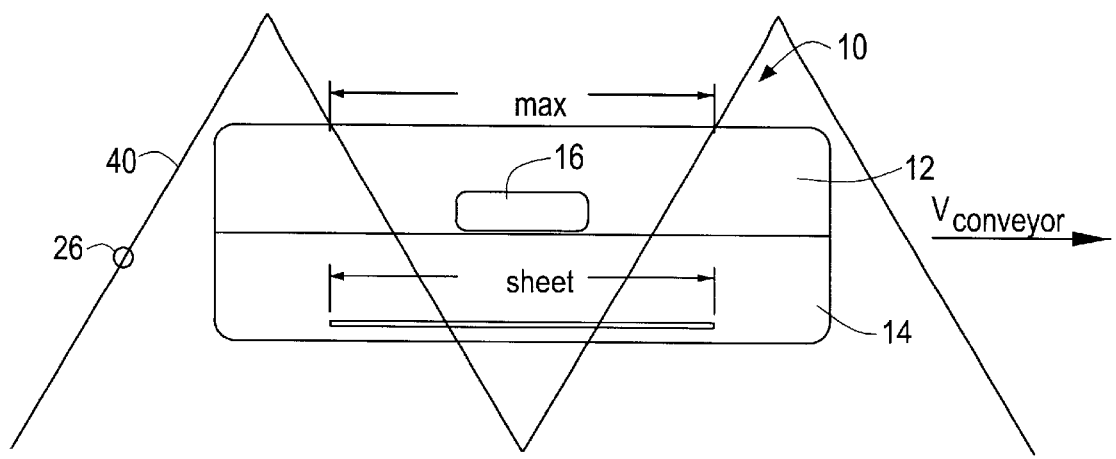
FIG. 6 is a view similar to FIGS. 1–5 illustrating the timing considerations to insure sheet interception of the X-ray scan with the movable X-ray scanner according to this invention.

Typically the conveyor carrying the suitcases will move at a rate of 20–40 cm/sec as shown by arrow 31, FIG. 5. Thus the reciprocating motion of source 26, FIG. 4, in the direction 28 must occur frequently enough so that at least one scan of sheet 20 will occur before the suitcase gets past the vertically reciprocating source. For example, scans occurring at 36 and 38, FIG. 5, would suffice. The criteria for determining this is shown in FIG. 6 where the path 40 of source 26 is shown as a sawtooth when viewed by the suitcase 10 which is passing by source 26. In that case, if sheet 20 has a length l then the maximum length between scans across the width of the suitcase $l_{max}$ can be no more than the length of the sheet $l_{sheet}$.

$$l_{max} = \frac{V_{conv} \times \tau_{time\ of\ reciprocation}}{2} \quad (1)$$

or, $$\frac{1}{\tau} = f_{scan\ freq} = \frac{v}{2 l sheet} \quad (2)$$

which typically turns out to be about 1 cycle per second for the reciprocation of the source for a conveyor that is moving at approximately 20–40 cm/sec.

Figure 7:
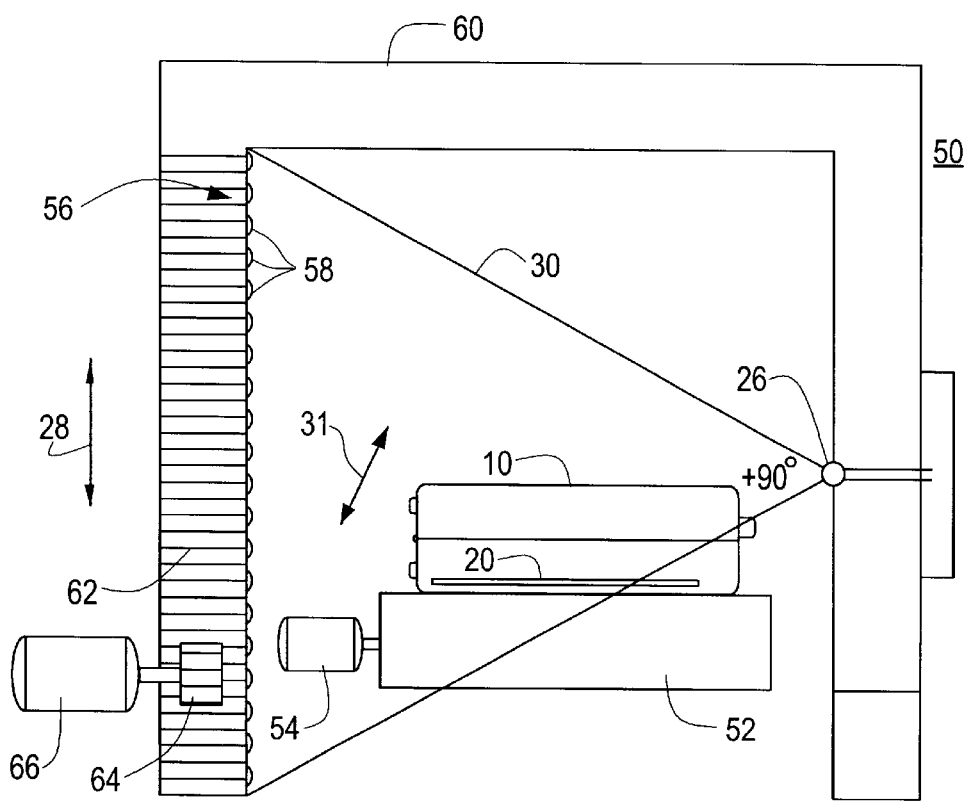
FIG. 7 is a schematic end view of a sheet detection system according to this invention in which both the X-ray source and the detectors are moved.

A detection system 50, FIG. 7, according to this invention includes some means, such as conveyor 52 driven by motor 54 for moving a container or suitcase 10 along a path past an X-ray scanner. The X-ray scanner may include a source 26 which provides a fan-shaped beam 30 and a detector 56 which includes a plurality of individual detector elements 58. Source 26 and detector elements 58 are both mounted on a support or frame 60 which has some means for shifting or moving frame 60 up and down, for example, a rack 62 engaged with pinion 64 driven by motor 66. In this way, at some point in the reciprocating motion 28 of frame 60 a beam of X-ray energy from source 26 will align with sheet 20.

Figure 8:
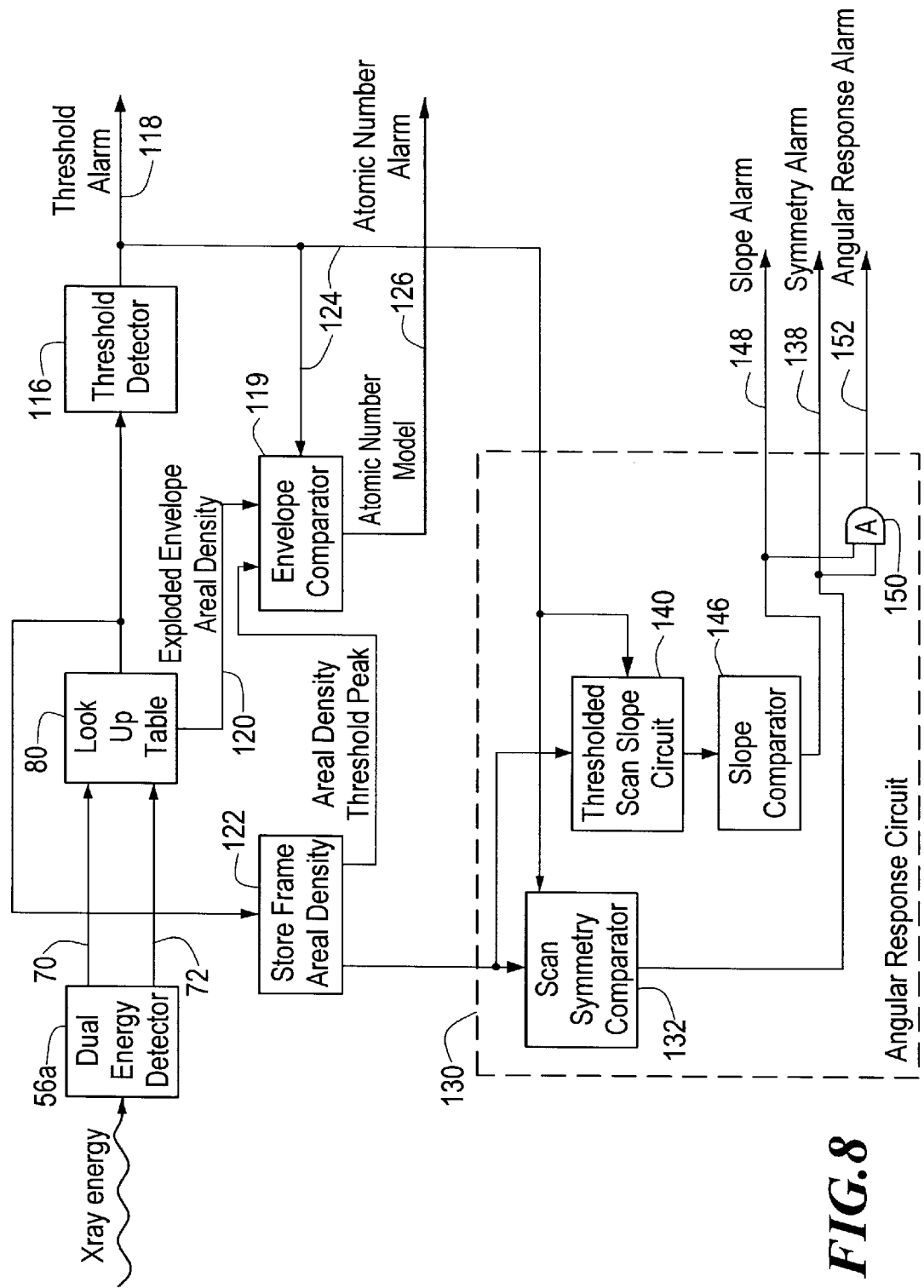
FIG. 8 is a functional block diagram of a sheet detection system according to this invention.
Figure 9:
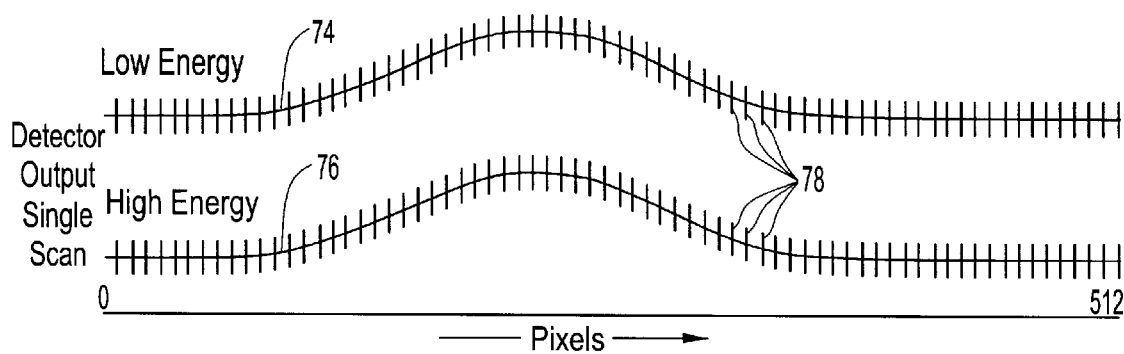
FIG. 9 is an illustration of the low energy and high energy output waveforms of the dual energy detector of FIG. 8.

Typically detector 56 is a dual energy detector 56a, FIG. 8, as is known which detects two different energy levels of incoming X-rays, for example, one at 40 Kev and one at 90 Kev, which are provided on lines 70 and 72. These two signals would appear as low energy 74 and high energy 76 waveforms, FIG. 9, which are composed of, for example, 512 data points 78 from 512 individual detector cells 58. The low energy 70 and high energy 72 signals are presented to look-up table 80, FIG. 8, which in turn produces an organic areal density corresponding to those energy levels if they are within a target envelope.

Figure 10:
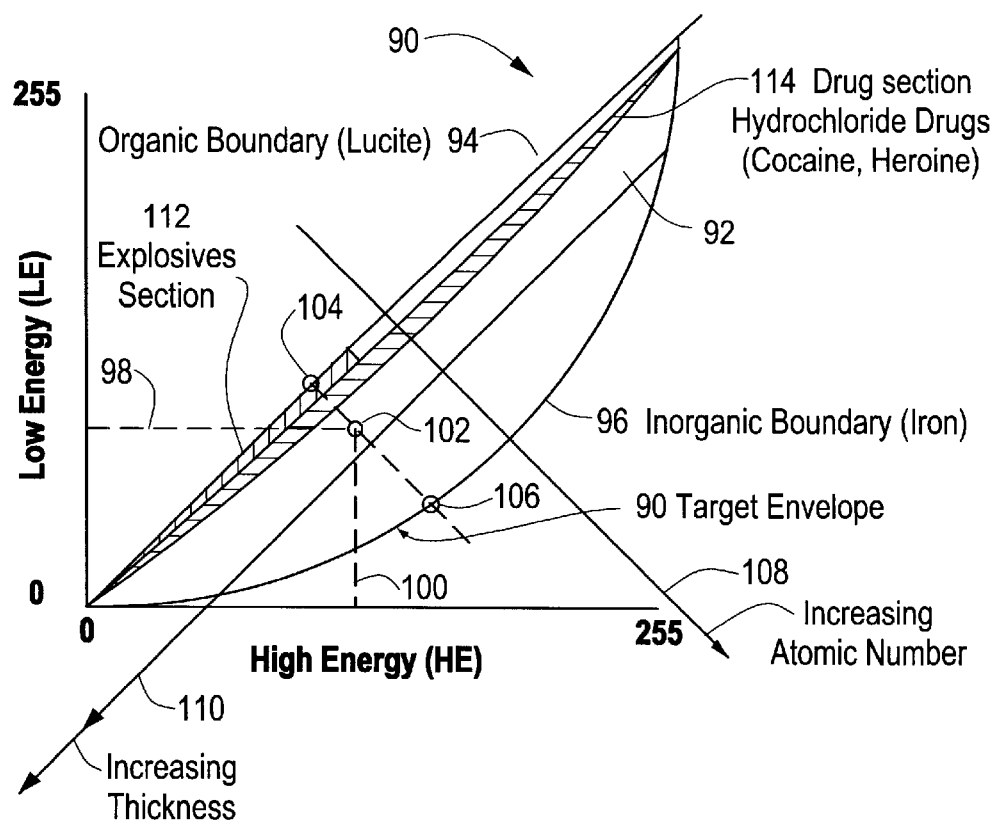
FIG. 10 is a graphical illustration of projected or areal densities in the target envelope stored in the look up table of FIG. 8.

The target envelope 90, FIG. 10, which defines the values stored in look-up table 80, is the area 92 between the organic boundary 94 obtained empircally by passing X-rays through a lucite sample, and an inorganic boundary 96 obtained by passing X-rays through an iron sample. All values between these two extremes can be considered to be a combination of some amount of lucite with some amount of iron. This is called basis vector decomposition as explained in Alvarez et al., U.S. Pat. No. 4,029,963. Low energy level 98 and high energy level 100 define a point 102 which represents the total transmitted energy of the object. The line connecting points 104 and 106 and intersecting 102 represent all of the low energy and high energy signals which have the same sum (low plus high or total energy transmitted). However, each point on this line represents a different amount of overlapping lucite and iron. Point 104 represents a low energy and high energy combination that can only be reached by a totally organic target. Point 106 can only be reached by a totally iron target. Point 102 can only be reached by a combination of lucite and iron. The output values at each location in the lookup table are those projected amounts of iron and lucite that can make up that combination of high energy and low energy. The output of 80 that goes to the threshold detector 116 of FIG. 8 is simply the lucite component and is referred to as the projected organic density. In addition Look Up Table 80 has for each point an effective atomic number which is another equivalent representation of the high energy and low energy signals. Within target envelope 90 the atomic number of the material increases from the organic boundary to the inorganic boundary as indicated by vector 108 and an increasing thickness of the material detected increases generally parallel to the organic boundary 94 as indicated by vector 110. Within target envelope 90 different define specific materials. For example, the cross-hatched area 112 represents plastic explosives whereas section 114 represents hypochloride based drugs such as cocaine and heroin.

Having determined the particular areal density, this value is delivered to threshold detector 116, FIG. 8, which determines whether the value exceeds a predetermined threshold. If it does, a threshold alarm is provided at output 118.

Another alarm can be derived by determining whether the atomic number of the material detected matches that of a particular contraband or material sought to be detected. For example, envelope comparator 119 can be triggered upon the detection of an areal organic density exceeding a predetermined threshold to provide a comparison between the effective atomic number of that thresholded signal with that of the atomic numbers in the explosive sector 112, FIG. 10. This is accomplished by using the store frame equivalent atomic number circuit 122 which stores the equivalent atomic number output from look-up table 80 for each scan in the frame. Thus when threshold detector 116 indicates that it has seen a threshold exceeded, a signal on line 124 causes envelope comparator 119 to compare the equivalent atomic number of the signal that exceeded the threshold with the explosive sector 112 of FIG. 10, as provided by a signal on line 120 shown in FIG. 8. If the effective atomic number of that detected signal is within the explosive sector then an atomic number alarm is provided on line 126. In some cases the measured atomic number will need to be corrected for the background on either spatial side of the thresholded peak. This can be done because the store frame circuit contains the full scan.

Figure 13:
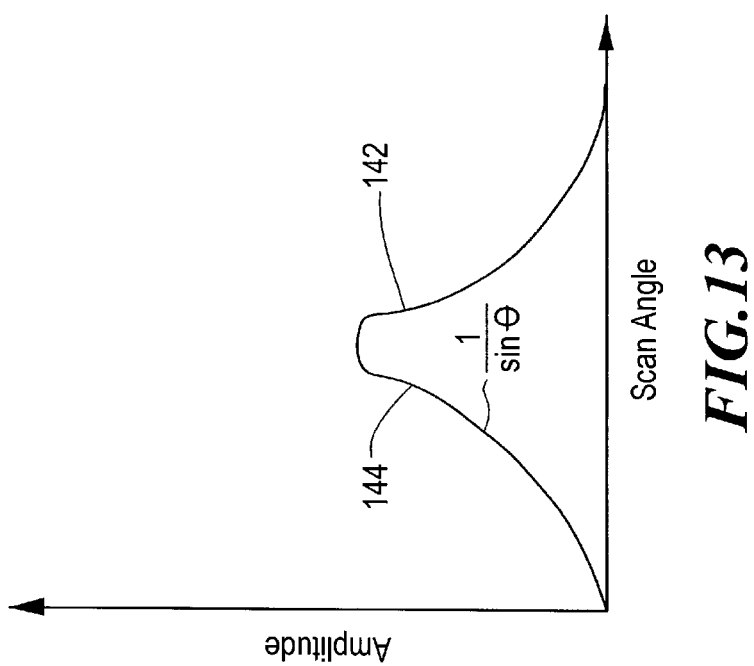
FIG. 13 is an illustration of the variation of amplitude with scan angle for a set of scans comprising a frame.
Figure 11:
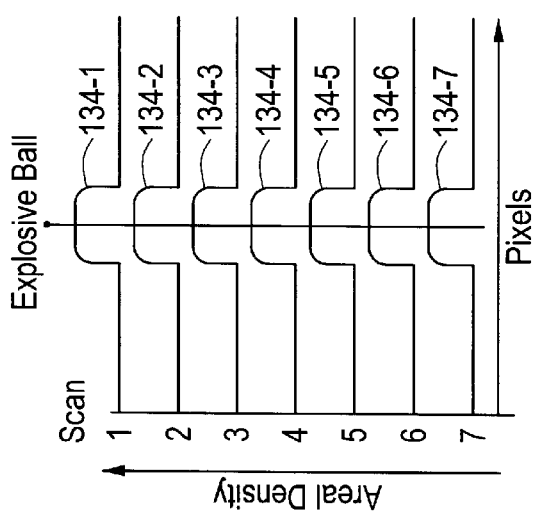
FIG. 11 is an illustration of the variation in areal density over a number of scans of a compact mass of material sought to be detected.
Figure 12:
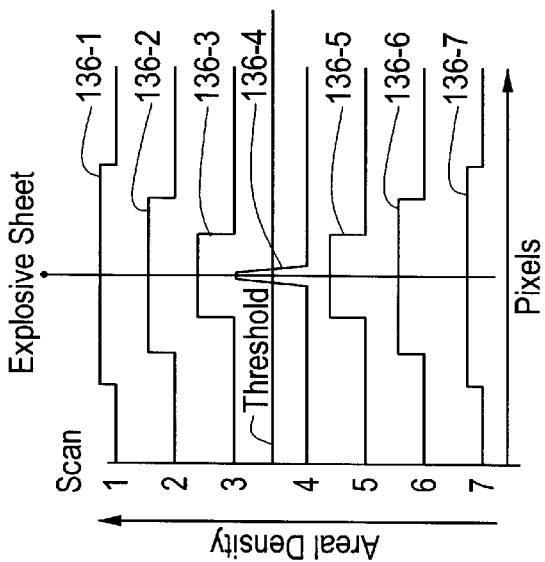
FIG. 12 is an illustration of the variation in areal density over a number of scans of a sheet of material sought to be detected.

A third alarm can be generated using an angular response circuit 130, FIG. 8. A scan symmetry comparator 132 compares the signal from each scan in a frame, where a frame includes all the scans for one excursion of the source movable with frame 60, FIG. 7. Typically a massive explosive in the form of a ball or a lump, FIG. 11, has a similar areal density profile along the pixels of the detector for each of the scans. For example, a frame including seven scans, shows an areal density profile 134-1 through 134-7 for each scan. However, when the explosive is in the form of a sheet the detector produces a profile which begins low and broad 136-1, becomes somewhat narrower and taller 136-2 in the second scan, even taller and narrower in the third scan 136-3, and finally peaks sharply 136-4 when the edge-on view occurs. Then as the source continues to move and the edge-on view dissipates, the profile begins to drop and broaden as shown at 136-5, 136-6 and 136-7 so that the leading and lagging scans appear generally symmetrical. Scan symmetry comparator 132 compares these profiles 136-1, 136-2 and 136-3 with profiles 136-7, 136-6 and 136-5, respectively, and if symmetry is found a symmetry alarm is provided on line 138. A separate alarm can be generated by angular response circuit 130 using the thresholded scan slope circuit 140. Thresholded scan slope circuit 140 calculates the slope of the scans 136-1 through 136-7 as shown in FIG. 13, where the characteristic 142 of amplitude versus scan angle is shown. If the slope at 144 as determined by slope comparator 146 has a predetermined value, for example, $1/\sin\theta$, then a slope alarm signal is provided on line 148. The slope alarm and symmetry alarm may be used conjunctively by means of AND circuit 150 to provide an angular response alarm on line 152 when both the slope and symmetry alarms are present. Scan symmetry comparator 132 and thresholded scan slope circuit 140 may be triggered to operate only upon the receipt of a signal on line 124 indicating that a signal has exceeded the threshold as determined by threshold detector 116.

Figure 14:
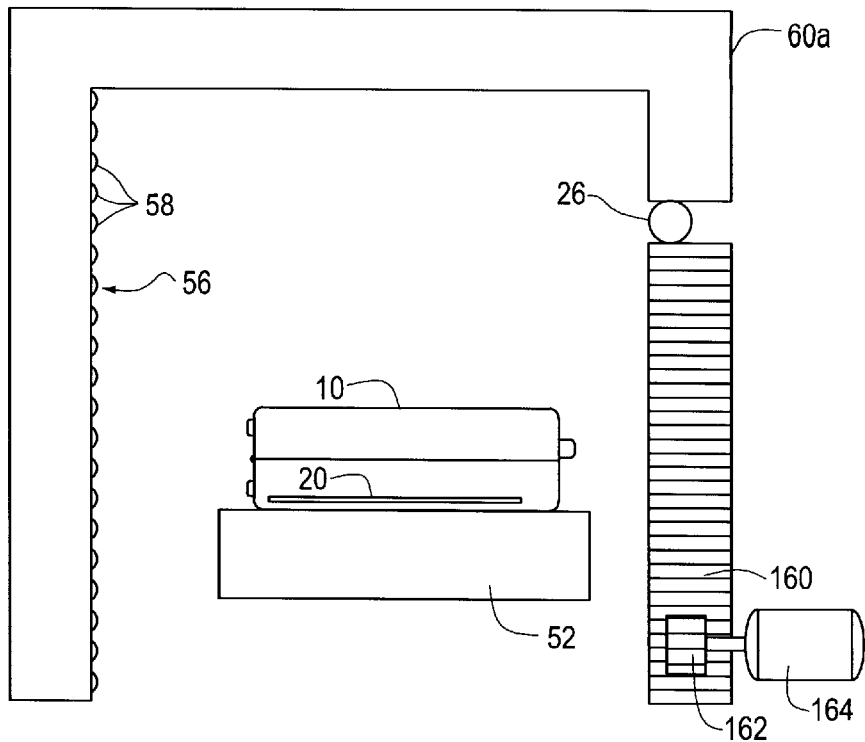
FIG. 14 is a view similar to FIG. 7 in which the detectors are stationary and the X-ray source is movable.
Figure 15:
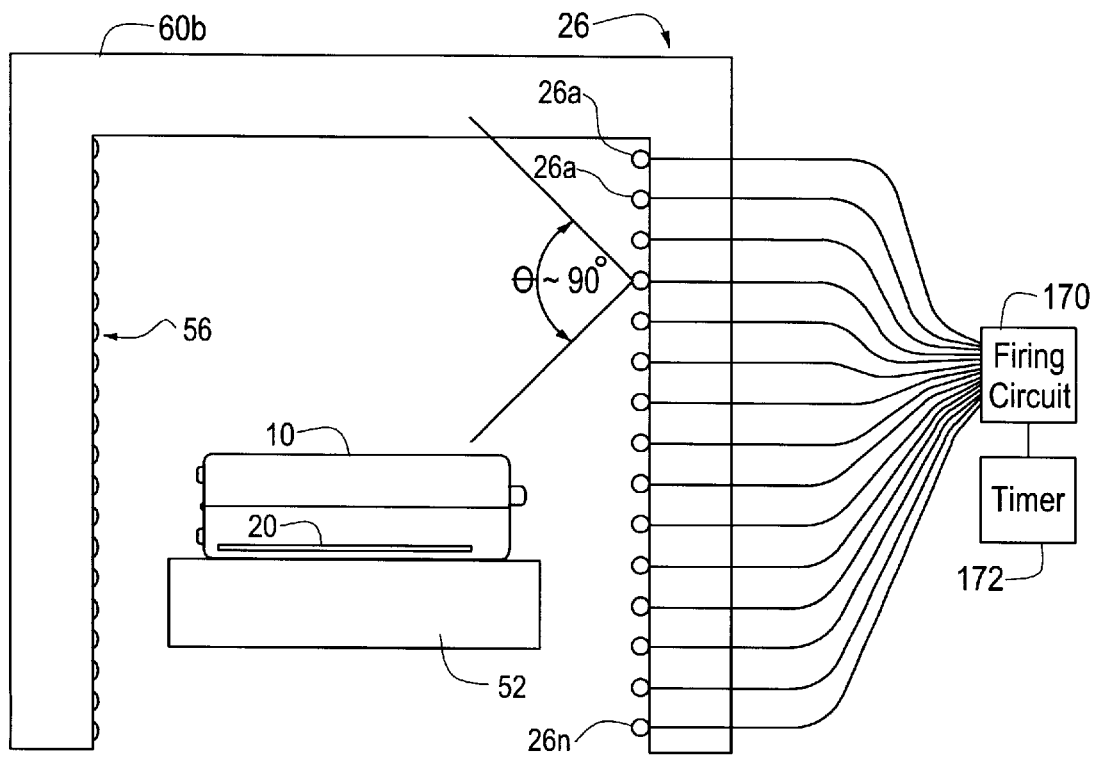
FIG. 15 is a view similar to FIGS. 7 and 14 in which the detectors are stationary and a plurality of X-ray sources are fired in sequence to move the X-ray scanning beam origin.
Figure 16:
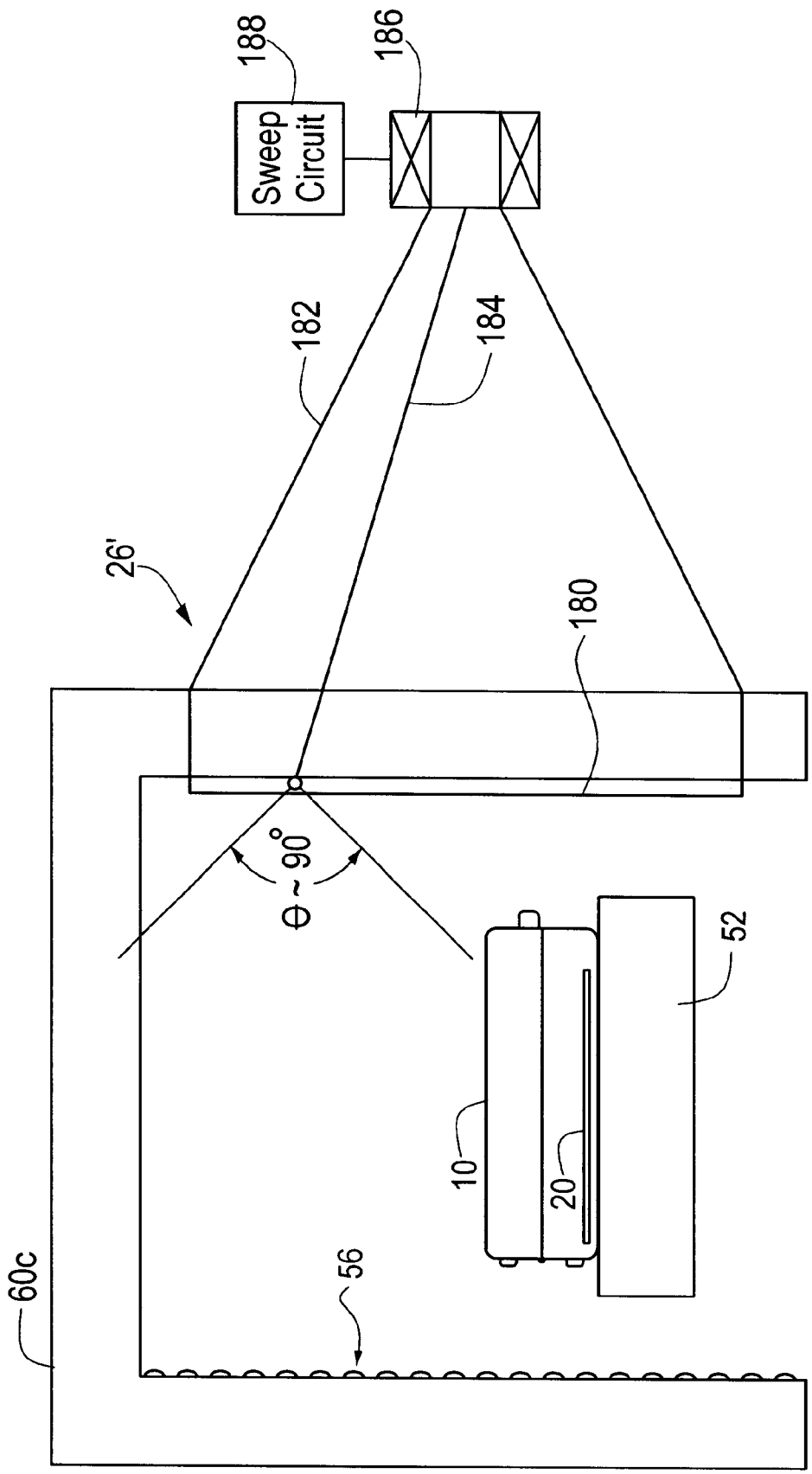
FIG. 16 is a view similar to FIGS. 7, 14 and 15 in which the detectors are stationary and an X-ray anode is sequentially energized by a sweeping electron beam to move the scanning X-ray beam origin.

Although thus far the means for shifting the scanner to move the origin has been shown as including a frame which moves both the detectors and the source, this is not a necessary limitation of the invention. For example, as shown in FIG. 14, the detector 56 may be stationary and frame 60a may contain only the X-ray source 26 which is driven by means of a rack 160 and pinion 162 operated by motor 164. The detector 56 can be stationary and the X-ray source 26 may be composed of a number of individual X-ray sources 26a–n, FIG. 15, which are fired in sequence (shifted) by firing circuit 170 operated by timer 172. In another construction detector 56 and X-Ray source 26' may be stationary and source 26' may be implemented using a linear anode 180 in the face of an electron beam scanner such as CRT 182 which provides a vertically scanning electron beam 184 driven (shifted) by coils 186 operated by sweep circuit 188.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A detection system for detecting sheets of material comprising:
   means for moving along a path a container which can harbor a sheet of material;
   an X-ray scanner having a scanning beam for scanning across the path of said container through a predetermined angle; and
   means for shifting the origin of said scanning beam to align during at least a portion of the scan said scanning beam with a sheet for producing a high projected density contrast with its surroundings.

2. The detection system of claim 1 in which said X-ray scanner includes an X-ray source and a spaced detector and said means for shifting includes a movable member for supporting said source and detector.

3. The detection system of claim 1 in which said X-ray scanner includes an X-ray source and a spaced detector and said means for shifting includes a movable member for supporting said source.

4. The detection system of claim 1 in which said X-ray scanner includes an X-ray source including a plurality of individual sources and said means for shifting includes means for sequentially enabling said individual sources.

5. The detection system of claim 1 in which said X-ray scanner includes a linear X-ray anode and said means for shifting includes means for sweeping an electron beam across said anode for generating a series of spaced X-ray scanning beams.

6. The detection system of claim 1 in which said X-ray scanner includes a detector for detecting X-ray energy transmitted by the sheet.

7. The detection system of claim 6 in which said detector includes a dual energy detector for detecting high and low X-ray energies.

8. The detection system of claim 6 in which said X-ray scanner provides a fan beam of X-ray energy.

9. A detection system for detecting sheets of material comprising:
   means for moving along a path a container which can harbor a sheet of material;
   an X-ray scanner having a scanning beam for scanning across the path of said container through a predetermined angle;
   means for shifting the origin of said scanning beam to align during at least a portion of the scan said scanning beam with a sheet for producing a high projected density contrast with its surroundings;
   a detector for detecting X-ray energy transmitted by the sheet; and
   means for determining whether the X-ray energy transmitted by the sheet represents an areal density within a target envelope of areal densities.

10. The detection system of claim 9 in which said X-ray scanner includes a threshold detector for determining whether the areal density representative of a sheet exceeds a predetermined level.

11. The detection system of claim 10 in which said X-ray scanner includes an envelope comparator for determining whether the areal density which exceeds said threshold represents an atomic number indicative of a sheet of particular material sought.

12. The detection system of claim 9 in which said means for determining includes a look up table of stored areal densities within the target envelope.

13. The detection system of claim 9 in which said X-ray scanner includes a storage device for storing areal densities representing a set of scans of the sheet.

14. The detection system of claim 13 in which said X-ray scanner includes an angular response circuit for determining the angular response of a set of scans.

15. The detection system of claim 14 in which said X-ray scanner includes means for determining whether the X-ray energy detected from the sheet represents an areal density within a target envelope of areal densities.

16. The detection system of claim 15 in which said angular response circuit includes means for determining symmetry in the areal density of the scans surrounding a scan which exceeds said thresholded level to confirm the presence of a sheet.

17. The detection system of claim 15 in which said angular response circuit includes means for determining the slope of the angular response of the areal densities of a set of scans indicative of the presence of a sheet of material.

18. An X-ray scanning system for detecting sheets of material in a container moving along a path, the system comprising:
   an X-ray source having a scanning beam for scanning across the path of the container through a predetermined angle, said X-ray source being movable relative to the path of the container to align said scanning beam with a sheet for producing a high projected density contrast with its surroundings.

* * * * *